United States Patent
Yokomizo et al.

(10) Patent No.: US 8,647,515 B2
(45) Date of Patent: Feb. 11, 2014

(54) BLOOD PROCESSING FILTER AND METHOD FOR PRIMING THE FILTER

(75) Inventors: Tomohisa Yokomizo, Tokyo (JP); Morikazu Miura, Tokyo (JP)

(73) Assignee: Asahi Kasei Medical Co,. Ltd., Tokyo (JP)

(*) Notice: Subject to any disclaimer, the term of this patent is extended or adjusted under 35 U.S.C. 154(b) by 50 days.

(21) Appl. No.: 13/252,288

(22) Filed: Oct. 4, 2011

(65) Prior Publication Data

US 2012/0160782 A1    Jun. 28, 2012

Related U.S. Application Data

(60) Provisional application No. 61/427,303, filed on Dec. 27, 2010.

(51) Int. Cl.
*B01D 37/00* (2006.01)
*B01D 35/00* (2006.01)

(52) U.S. Cl.
USPC ............................ 210/767; 210/435; 210/450

(58) Field of Classification Search
USPC ......... 210/645, 650, 767, 232, 435, 445, 450, 210/453, 461, 483
See application file for complete search history.

(56) References Cited

U.S. PATENT DOCUMENTS

| | | |
|---|---|---|
| 6,601,710 B2 | 8/2003 | Calhoun et al. |
| 2001/0037978 A1 | 11/2001 | Calhoun et al. |
| 2002/0063090 A1 | 5/2002 | Calhoun et al. |
| 2004/0251195 A1 | 12/2004 | Oka et al. |

FOREIGN PATENT DOCUMENTS

| | | |
|---|---|---|
| EP | 526678 | 2/1993 |
| JP | 1-320064 | 12/1989 |
| JP | 7-267871 | 10/1995 |
| JP | 2002-541941 | 12/2002 |
| JP | 2004-173853 | 6/2004 |
| JP | 2007-253374 | 10/2007 |

(Continued)

OTHER PUBLICATIONS

English translation Japanese Patent Application No. 2007-254473 A.*

(Continued)

*Primary Examiner* — John Kim
(74) *Attorney, Agent, or Firm* — Greenblum & Bernstein P.L.C.

(57) ABSTRACT

This invention relates to a blood processing filter including a sheet-like filter element and a flexible container having an internal space divided by the filter element. The container includes first and second container-forming-parts. The first container-forming-part includes an interior filtration space-forming-part and an exterior surrounding space-forming-part that are separated by a first seal-part. The second container-forming-part includes an extension space-forming-part surrounded by the second seal-part and arranged opposite the filter element and the surrounding space-forming-part, without being divided by the first seal-part. A port of the first container-forming-part is provided in the filtration space-forming-part and communicates with an internal space on one side defined by the filter element. The port of the second container-forming-part is provided in the extension space-forming-part and communicates with an internal space on another side defined by the filter element, and protrudes further than an outer surface of the extension space-forming-part.

5 Claims, 10 Drawing Sheets

(56) References Cited

FOREIGN PATENT DOCUMENTS

| WO | 92/20428 | 11/1992 |
| WO | 95/17236 | 6/1995 |
| WO | 01/91880 | 12/2001 |
| WO | 02/04045 | 1/2002 |
| WO | 2004/050147 | 6/2004 |

OTHER PUBLICATIONS

Search report from P.C.T., mail date is Dec. 20, 2011.
U.S. Appl. No. 13/334,226, to Tomohisa Yokomizo et al., filed Dec. 22, 2011.
International Preliminary Report on Patentability for PCT/JP2011/072459, mailed Jul. 11, 2013.

* cited by examiner

BLOOD PROCESSING FILTER AND METHOD FOR PRIMING THE FILTER

CLAIM FOR PRIORITY

This application claims the priority benefit of U.S. Provisional Application No. 61/427,303, filed Dec. 27, 2010, the contents of which is expressly incorporated by reference in its entirety.

BACKGROUND OF THE INVENTION

1. Field of the Invention

The present invention relates to a blood processing filter for removing undesirable components such as aggregates and leukocytes from blood. In particular, the present invention relates to a precise and disposable blood processing filter for removing microaggregates and leukocytes which may cause side effects from whole blood preparations, erythrocyte preparations, thrombocyte preparations, blood plasma preparations and the like for blood transfusion, as well as a method for priming the blood processing filter.

2. Related Background Art

It is becoming common for whole blood collected from a donor to be separated into blood component preparations such as an erythrocyte preparation, a thrombocyte preparation, and a blood plasma preparation and stored for transfusion. Since microaggregates and leukocytes included in these blood preparations cause various side effects during blood transfusion, the number of occasions for removing these undesirable components before blood transfusion has been increasing. The need for leukocyte removal has widely been recognized particularly in recent years. Legislation regarding removal of leukocytes from all kinds of blood preparations for blood transfusion before being used for transfusion has been introduced in an increasing number of countries.

The most common method of removing leukocytes from blood preparations is by processing blood preparations using a leukocyte removal filter. Conventionally, in many cases blood preparations processed using a leukocyte removal filter have been processed at the bedside when blood transfusion is performed. In recent years, however, to improve quality control of leukocyte-free preparations and efficiency of leukocyte removal operations, it is more common, particularly in developed countries, to process the blood preparations in blood centers before storing the blood preparations. Hereinafter, a leukocyte removal performed before storage is referred to as a "pre-storage leukocyte removal".

A blood collection-separation set, typically consisting of two to four flexible bags, a tube connecting these bags, an anticoagulant, an erythrocyte preservation solution, a blood collection needle, and the like has been used for collecting blood from a donor, separating the blood into several blood components, and storing the blood components. A system in which a leukocyte removal filter is incorporated into such a blood collection-separation set has been widely used as an optimum system for the above-mentioned "pre-storage leukocyte removal". Such a system is called a "closed system" or an "integrated system" or the like. Such systems are disclosed in Japanese Patent Laid-Open No. 1-320064, International Publication No. WO 92/020428 and the like.

Conventionally, a filter element made from nonwoven fabric or a porous body packed in a hard container of polycarbonate or the like has been widely used as a leukocyte removal filter. However, because, in case of the hard container, the container has a low level of air permeability, there is the problem that it is difficult to apply steam sterilization, which is widely used as a sterilization process in blood collection-separation sets. In one type of closed system, leukocytes are first removed from the whole blood preparation after collecting the blood. Subsequently, after the leukocyte removal filter is separated, the leukocyte-free blood is centrifuged for separation into various components. In another type of closed system, the whole blood is first centrifuged to be divided into various blood components, and then the leukocytes are removed. In the latter system, the leukocyte removal filter is also centrifuged together with the blood collection-separation set. At such time, a hard container may damage bags and tubes, or the hard container itself may not withstand the stress and may break during centrifugation.

To solve these problems, flexible leukocyte removal filters have been developed in which the container is made of a material having excellent flexibility and steam permeability that is the same as or similar to the material used for the bags of the blood collection-separation set, and in fact blood processing filters in which a flexible container is directly welded to a filter element and the like are known (see Japanese Patent Laid-Open No. 7-267871 and International Publication No. WO 95/017236). According to this kind of conventional blood processing filter, for example, a flexible container is formed using a sheet-like material having flexibility, and an internal space of the flexible container is divided into one side and another side by a filter element. Ports that serve as an inlet and an outlet for blood are respectively provided on the one side and the other side into which the flexible container is divided by the filter element.

However, according to the conventional leukocyte removal filter, in many cases the one side and the other side into which the flexible container is divided by the filter element are substantially the same shape and have the same capacity, and it can not be said that sufficient consideration has been given to filter performance in relation to suppressing blockage of the filter element that results from the interrelationship between the one side and the other side of the flexible container and to preventing an air block occurring when priming and the like.

SUMMARY OF THE INVENTION

An object of the present invention is to provide a blood processing filter that can improve the filter performance.

More specifically, according to the present invention, there is provided a blood processing filter that includes a sheet-like filter element, and a flexible container having an internal space that is divided into one side and another side by the filter element; the flexible container including: a first container-forming part and a second container-forming part that are arranged opposite each other so as to sandwich the filter element therebetween; ports provided in the first container forming part and the second container forming part, respectively, that serve as an inlet or an outlet for blood; a band-shaped annular first seal part that seals the first container forming part and the filter element in a band shape, and that is formed so as to surround the port provided in the first container forming part; and an annular second seal part that seals at least the first container forming part and the second container forming part, and that is formed so as to surround the first seal part along an outer edge of the second container forming part; wherein: the first container forming part has an interior filtration space forming part and an exterior surrounding space forming part that are separated by the first seal part; the second container forming part has an extension space forming part that is surrounded by the second seal part and is arranged opposite the filter element and the surrounding space forming part, without being divided by the first seal part; the port of the first container forming part is provided in the filtration space forming part and communicates with an internal space on the one side that is defined by the filter element; and the port of the second container forming part is provided in the extension space forming part and communicates with an internal space on the other side that is defined by the filter element, and protrudes further than an outer surface of the extension space forming part. In this connection, in the present invention the term "blood" includes blood preparations such as whole blood preparations, erythrocyte preparations, thrombocyte preparations, and blood plasma preparations for blood transfusion.

In the above described blood processing filter, an area surrounded by the first seal part of the filter element functions as an effective filtering portion of the filter element. Further, with respect to the internal space of the flexible container, a space on one side is a narrow space that substantially faces the effective filtering portion, and a space on the other side is a wide space that includes not only a narrow space that faces the effective filtering portion but also a surrounding extended space. Accordingly, when the blood processing filter is used so that the wide space side serves as an outlet side for blood, for example, it is possible to prevent an air block occurring due to a build-up of air bubbles at the surface on the outlet side of the filter element when priming the filter, and thereby improve the filter performance. Further, when the blood processing filter is used so that the wide space side serves as an inlet side for blood, for example, even if aggregates or air bubbles enter during filtration, the aggregates or air bubbles escape to the surrounding extended space that is located away from the effective filtering portion, and thus blockage of the filter element can be suppressed and filter performance can be improved.

The present invention can also provide a blood processing filter according to the above described blood processing filter, in which the port of the first container forming part is an inlet port that serves as an inlet for blood, and the port of the second container forming part is an outlet port that serves as an outlet for blood.

When performing priming with respect to the above described blood processing filter, the blood processing filter is set on a mounting face in a state in which the outlet side is facing downward. Since the outlet port that protrudes from the outer surface of the extension space forming part is provided in the blood processing filter, when the blood processing filter is set on the mounting face in a state in which the outlet side is facing downward, the outlet port comes between the outer surface and the mounting face, and the blood processing filter enters an inclined state. As a result, a portion of a surrounding space forming part that encloses the filtration space forming part in an annular shape is positioned at a higher position than the filtration space forming part. Next, a priming fluid is filled from the outlet port of the blood processing filter. The boundary surface of the priming fluid rises as the priming fluid is filled, and as a result the air on the outlet side passes through the filter element and is pushed out from the inlet port. At this time, some air remains inside the space on the outlet side of the filter element. However, since a space for accumulating air that is formed by the surrounding space forming part exists in an upper part on the outlet side, the residual air escapes into the space for accumulating air, and thus the occurrence of an air block inside the space on the outlet side that corresponds to the filtration space forming part can be suppressed and removal of air can be performed smoothly.

Further, the present invention can provide a blood processing filter according to the above described blood processing filter, in which the port of the first container forming part is an outlet port that serves as an outlet for blood, and the port of the second container forming part is an inlet port that serves as an inlet for blood.

According to this blood processing filter, for example, even when blood with respect to which generation of aggregates is a concern is processed, such as when the blood has been stored in refrigerated storage for a fixed period of time, since a wide space is formed on the inlet side, the possibility of aggregates and the like attaching to the filter element and blocking the filter element can be reduced.

The present invention can also provide a blood processing filter according to the above described blood processing filter, in which, the outlet port is arranged in a region of the extension space forming part that overlaps with the filtration space forming part.

Further, the present invention can provide a blood processing filter according to the above described blood processing filter, in which the inlet port and the outlet port are point symmetric.

In addition, the present invention relates to a method for priming a blood processing filter including a sheet-like filter element, and a flexible container having an internal space that is divided into one side and another side by the filter element. In particular, the flexible container of the blood processing filter used in the priming method includes: a first container forming part and a second container forming part that are arranged opposite each other so as to sandwich the filter element therebetween, an inlet port that is provided in the first container forming part and that serves as an inlet for blood, an outlet port that is provided in the second container forming part and that serves as an outlet for blood, a band-shaped annular first seal part that seals the first container forming part and the filter element and that is formed so as to surround the inlet port, and an annular second seal part that seals at least the first container forming part and the second container forming part and that is formed so as to surround the first seal part along an outer edge of the second container forming part; wherein: the first container forming part has an interior filtration space forming part and an exterior surrounding space forming part that are separated by the first seal part, and the second container forming part has an extension space forming part that is surrounded by the second seal part and is arranged opposite the filter element and the surrounding space forming part, without being divided by the first seal part; and the inlet port is provided in the filtration space forming part and communicates with an internal space on the one side that is defined by the filter element, and the outlet port is provided in the extension space forming part and communicates with an internal space on the other side that is defined by the filter element and protrudes further than an outer surface of the extension space forming part. The priming method can be related to a priming method including: a step of turning the blood processing filter sideways with the outlet port facing downwards, and setting the blood processing filter on a mounting face in a state in which the blood processing filter is inclined with respect to the mounting face; and a step of filling a priming fluid from the outlet port of the blood processing filter that is set on the mounting face to remove air from inside the blood processing filter.

DESCRIPTION OF THE PREFERRED EMBODIMENTS

Embodiments of the present invention are described hereunder with reference to the drawings. Note that the term "blood" that is described in the following embodiments includes blood preparations such as whole blood preparations, erythrocyte preparations, thrombocyte preparations and blood plasma preparations for blood transfusion. Further, although various forms can be adopted for the external shape of the blood processing filter, such as a rectangular shape, a disc shape, an oval disc shape, and an elliptical shape, a rectangular shape is preferable for decreasing loss of materials when the filters are manufactured. Accordingly, in the following embodiments, an example in which the blood processing filter has a rectangular shape is described.

Figure 1:
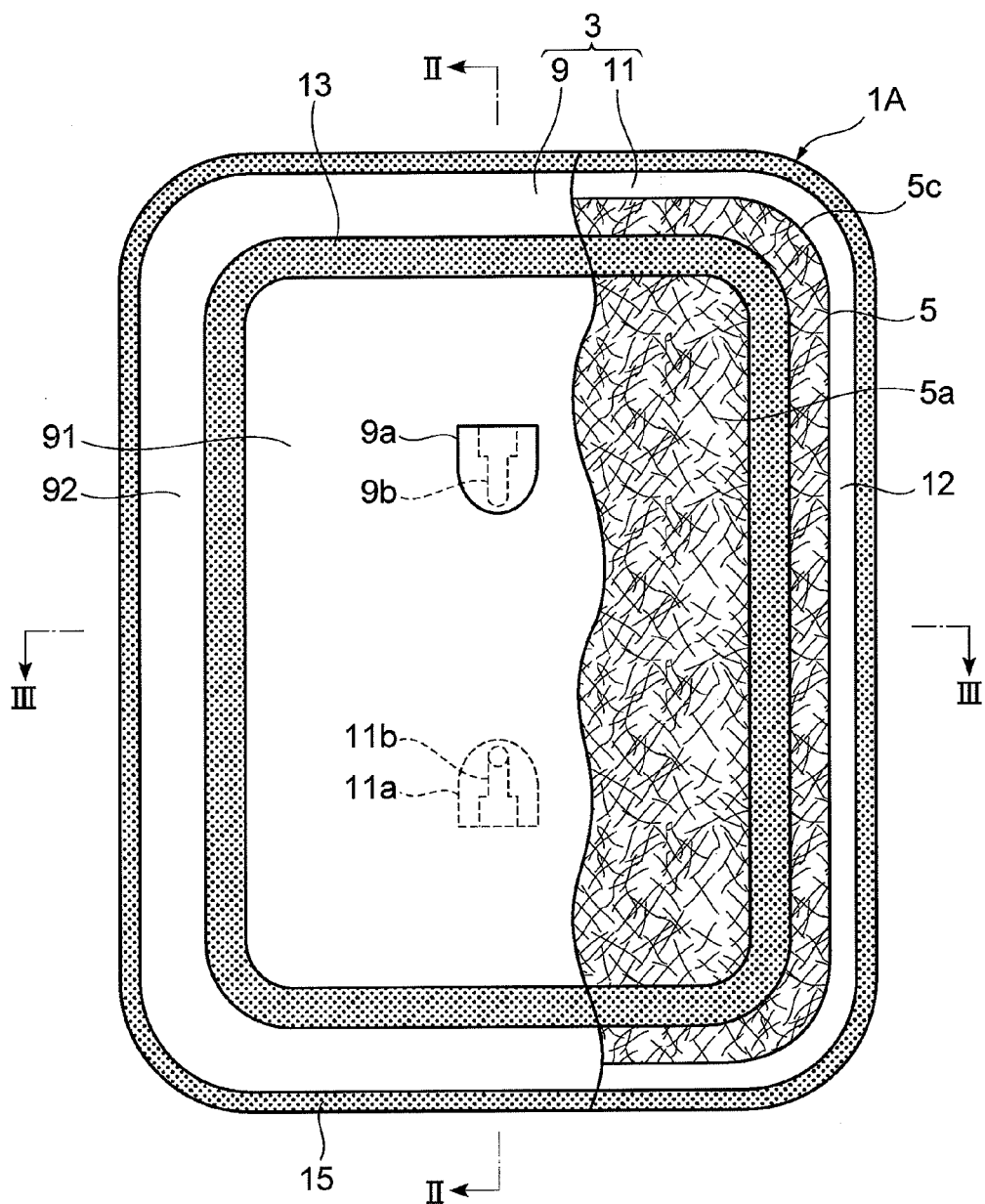
FIG. 1 is a plan view that illustrates one portion of a blood processing filter according to a first embodiment of the present invention, that is shown in a cut-away manner.
Figure 2:
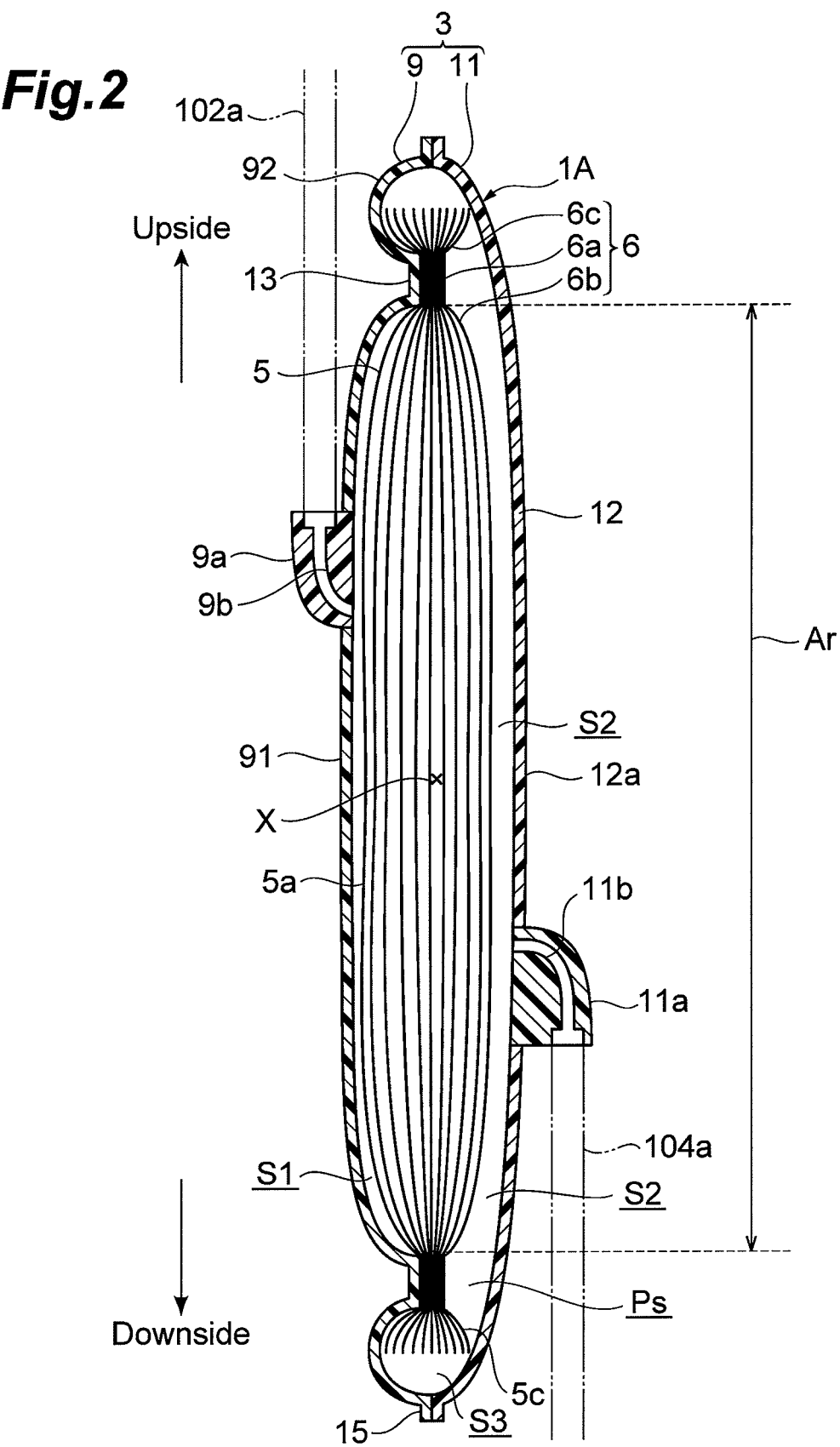
FIG. 2 is a sectional view taken along a line II-II in FIG. 1.
Figure 3:
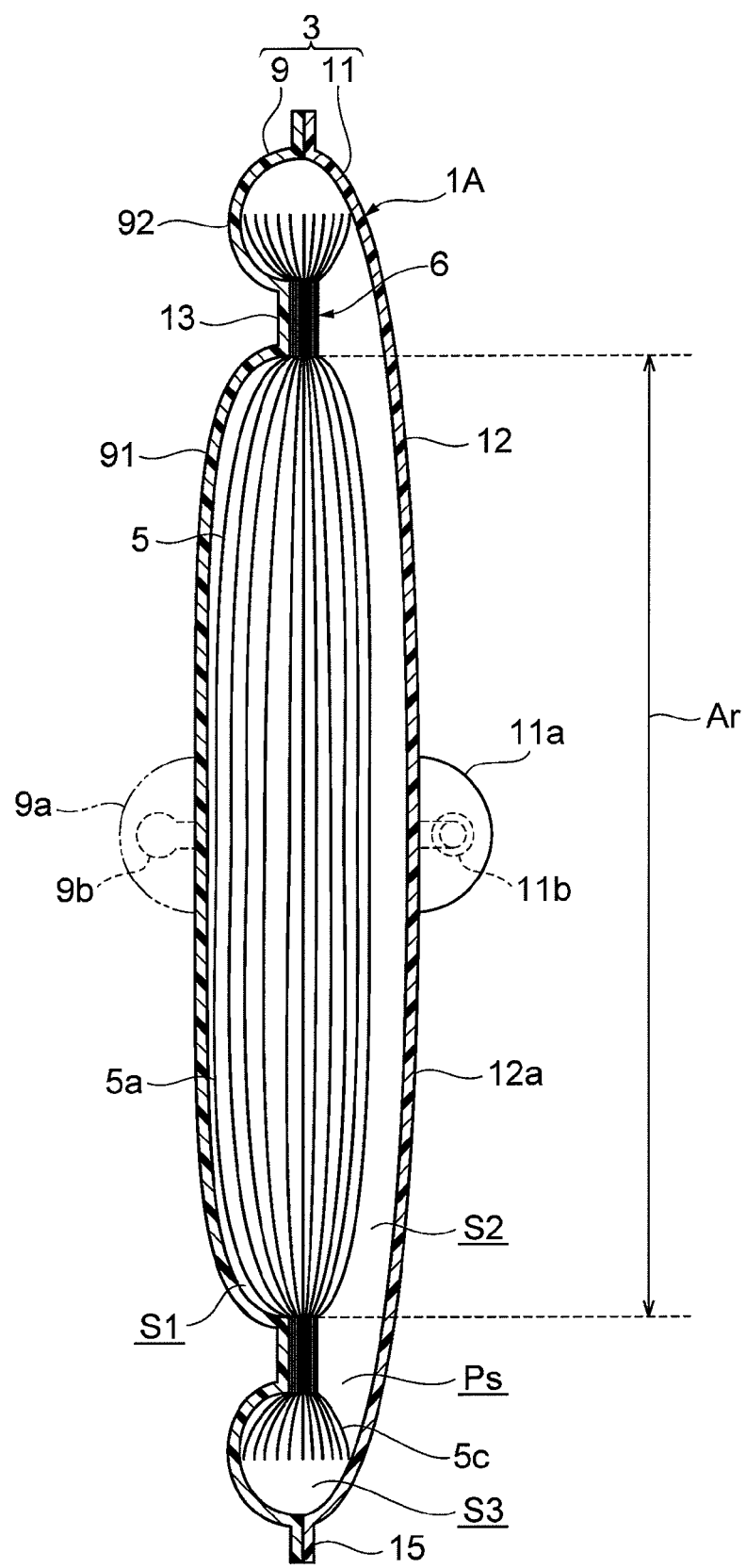
FIG. 3 is a sectional view taken along a line in FIG. 1.

First, a blood processing filter 1A according to a first embodiment of the present invention is described referring to FIGS. 1 to 3. The blood processing filter 1A includes a flexible container 3 having an inlet port 9a and an outlet port 11a for blood, and a sheet-like filter element 5 that is arranged so as to divide an internal space of the flexible container 3 into one side and another side. The inlet port 9a communicates with an internal space on the one side of the flexible container 3 whose internal space is divided into two sides by the filter element 5, and the outlet port 11a communicates with an internal space on the other side of the flexible container 3. The inlet port 9a and the outlet port 11a are arranged so that, when the approximate center of the filter element 5 is defined as a hypothetical point X, the inlet port 9a and the outlet port 11a are point symmetric about the hypothetical point X as the center.

The flexible container 3 has a rectangular, flat shape. Here, the term "flat shape" means a shape having a thin thickness and a wide surface. The flexible container 3 includes a first container forming part 9 that has a rectangular sheet shape, and a second container forming part 11 that has a rectangular sheet shape. The first container forming part 9 and the second container forming part 11 are arranged opposite each other so as to sandwich the filter element 5 therebetween.

An inlet port 9a in which an inlet flow channel 9b that allows the inside and the outside to communicate is formed is sealed in the first container forming part 9. The inlet port 9a is an inlet through which pre-processing blood is accepted into the internal space of the flexible container 3. An outlet port 11a in which an outlet flow channel 11b that allows the inside and the outside to communicate is formed is sealed in the second container forming part 11. The outlet port 11a is an outlet through which processed blood is discharged from the flexible container 3. In this connection, as used herein, the term "seal (to seal)" refers to fixing by bonding (including welding) to a degree that can prevent leakage of a liquid.

The first container forming part 9 is sealed along the periphery of the filter element 5 in a state in which the first container forming part 9 is adhered to the filter element 5. An area that is sealed in a band shape along the periphery of the filter element 5 is an inside seal part 13. The inside seal part 13 surrounds the inlet port 9a in a rectangular ring shape.

The first container forming part 9 is divided into an inner side that is surrounded by the inside seal part 13, and an outer side that encloses the inside seal part 13. An area located at a position that is further on the inner side than the inside seal part 13 is a filtration space forming part 91. The inlet port 9a is provided in the filtration space forming part 91. A filtration space S1 through which blood that has flown out from the inlet port 9a flows is formed between the filtration space forming part 91 and the filter element 5. A portion of the filter element 5 that faces the filtration space S1 is an effective filtering portion 5a. The inside seal part 13 corresponds to a first seal part. In this connection, a protruding nonwoven fabric portion 5c that is a surplus portion of the filter element 5 protrudes to the outside of the inside seal part 13.

The periphery of the first container forming part 9 overlaps with the periphery of the second container forming part 11, and the peripheries adhere with each other and are sealed in a band shape. An area that is sealed along the peripheries of the first container forming part 9 and the second container forming part 11 is an outside seal part 15 that surrounds the inside seal part 13 in a rectangular ring shape. An approximately donut-shaped area formed between the inside seal part 13 and the outside seal part 15 is a surrounding space forming part 92. The outside seal part 15 corresponds to a second seal part.

A rectangular ring-shaped recess that corresponds to the rectangular ring-shaped inside seal part 13 is formed on the outlet side of the filter element 5. This recess is formed as a result of the filter element 5 being integrated with the first container forming part 9 in a state in which the filter element 5 is compressed from both sides accompanying formation of the inside seal part 13. This recess is a valley part 6 that is provided on the outlet side of the filter element 5.

The valley part 6 will now be described in further detail (see FIG. 2). The filter element 5 that is formed by stacking a plurality of nonwoven fabrics or the like has a constant thickness, and in a state in which sealing such as welding has not been performed, the surface of the filter element 5 is in a flat state. Subsequently, for example, if the two faces of the filter element 5 are sandwiched with a PVC sheet and high frequency welding is performed, the welded place is crushed and integrated, and the integrated place is thin in comparison to the original thickness of the filter element 5.

According to the filter element 5 of the present embodiment, for example, a process for sealing, such as high frequency welding, is carried out using a predetermined mold to form the inside seal part 13, and as a result an integrated place is formed in a ring shape. The places other than the integrated place are still substantially flat over the entire area of the filter element 5 after the process for sealing has been carried out, and only the vicinity of the integrated place is different. For example, when attention is focused on the outlet side of the filter element 5, it is seen that the integrated place is a bottom part 6a that is the most recessed area, and areas adjoining the integrated place are slanted face portions 6b and 6c that rise almost perpendicularly from the bottom part 6a. More specifically, the valley part 6 has the bottom part 6a that overlaps with the inside seal part 13, the inner slanted face portion 6b that rises towards the inner side of the inside seal part 13 from the bottom part 6a, and the outer slanted face portion 6c that rises towards the outer side of the inside seal part 13 from the bottom part 6a.

Although the second container forming part 11 is integrated with the first container forming part 9 through the outside seal part 15, the second container forming part 11 is not bonded to the filter element 5, and in an at-rest state the second container forming part 11 enters a state in which the second container forming part 11 is roughly separated from the valley part 6 of the filter element 5. More specifically, the second container forming part 11 has an extension space forming part 12 that is arranged so that an area facing the filter element 5 and an area facing the surrounding space forming part 92 of the first container forming part 9 are formed in a continuous manner without being separated by the inside seal part 13.

A filtration space S2 is formed on the outlet side between the extension space forming part 12 and the filter element 5, and an air accumulating space S3 to which air escapes during priming is formed between the extension space forming part 12 and the surrounding space forming part 92. There is no partition between the filtration space S2 on the outlet side and the air accumulating space S3, and therefore the filtration space S2 and the air accumulating space S3 communicate with each other.

The outlet port 11a is provided in the extension space forming part 12 of the second container forming part 11, and protrudes further than an outer surface 12a of the extension space forming part 12. In particular, the outlet port 11a according to the present embodiment is arranged in a region Ar of the extension space forming part 12. The region Ar overlaps with the filtration space forming part 91 of the first container forming part 9.

Next, forms of the material and shape and the like of each element constituting the blood processing filter 1A are described. As described in the foregoing, the flexible container 3 is formed by the first container forming part 9 and the second container forming part 11. Any material that is commercially available as a sheet or a film can be used as a flexible resin that is used for the flexible container 3. For example, thermoplastic elastomers such as soft polyvinyl chloride, polyurethane, ethylene-vinyl acetate copolymer, polyolefin such as polyethylene and polypropylene, hydrogenated styrene-butadiene-styrene copolymer, styrene-isoprene-styrene copolymer, and hydrogenated products thereof, mixtures of the thermoplastic elastomer and a softening agent such as polyolefin and ethylene-ethyl acrylate, and the like may be mentioned as favorable materials. Since it can be considered that the material will contact with blood, preferable materials are soft polyvinyl chloride, polyurethane, and polyolefin that are used as the material of medical products such as blood bags, as well as thermoplastic elastomers containing these materials as main components, and more preferably the material is soft polyvinyl chloride.

Further, for example, a container described in Japanese Patent Laid-Open No. 7-267871 or a container described in International Publication No. WO 95/017236 can also be used as the flexible container 3.

The filter element 5 is manufactured using a filter material constituted by a fibrous integrated body such as nonwoven fabric or woven fabric or by a porous body such as sponge. The filter element 5 according to the present embodiment may be coated with a hydrophilic polymer to make it easier for blood to wet the filter material. Further, to facilitate attachment of leukocytes to the filter element 5 when using the blood processing filter 1A to remove leukocytes from blood, a filter material that is coated with a polymer may be used.

Next, a method for manufacturing the blood processing filter 1A according to the present embodiment is described. According to this manufacturing method, for example, the first container forming part 9 in which the inlet port 9a has been sealed at a predetermined position, the second container forming part 11 in which the outlet port 11a has been sealed at a predetermined position, and the filter element 5 are prepared, and an installing step is performed in which the first container forming part 9 and the second container forming part 11 are arranged at predetermined positions so as to sandwich the filter element 5.

After the installing step, a first sealing step and a second sealing step are performed without sealing the filter element 5 and the second container forming part 11. In the first sealing step, the inside seal part 13 is formed by sealing the first container forming part 9 and the filter element 5 in a band shape so as to surround the area in which the inlet port 9a is formed. In the second sealing step, the annular outside seal part (second seal part) 15 is formed by sealing the peripheries of the first container forming part 9 and the second container forming part 11 together in a band shape so as to surround the inside seal part 13.

In the first sealing step, the valley part 6 that has a band shape that corresponds to the inside seal part 13 is generated on the outlet side of the filter element 5. A passage region Ps is formed between the second container forming part 11 and the filter element 5 by the valley part 6. An inner area that is surrounded by the passage region Ps serves as the filtration space S2 on the outlet side, and an outer area serves as the air accumulating space S3.

Although formation of the inside seal part 13 in the first sealing step, more specifically, sealing of the first container forming part 9 and the filter element 5 can be performed utilizing high frequency welding, the present invention is not limited thereto, and various kinds of bonding techniques, such as ultrasonic welding and thermal welding, can be used.

Likewise, although formation of the outside seal part 15 in the second sealing step, more specifically, sealing of the first container forming part 9 and the second container forming part 11 can be performed utilizing high frequency welding, the present invention is not limited thereto, and various kinds of bonding techniques, such as ultrasonic welding and thermal welding, can be used.

According to the above described manufacturing method, a form is described in which the inlet port 9a is previously sealed to the first container forming part 9, and the outlet port 11a is previously sealed to the second container forming part 11. However, sealing may be performed after forming the inside seal part 13 or the outside seal part 15, or may be performed during the process of forming the inside seal part 13 or the outside seal part 15. Further, a method of sealing the inlet port 9a as a blood inlet and the outlet port 11a as a blood outlet to the flexible container 3 is not limited to high frequency welding, and various kinds of bonding techniques, such as thermal welding, can be used. Similarly to the flexible container 3, various known materials can be used as the material of the inlet port 9a and the outlet port 11a.

According to the above described manufacturing method, since the second container forming part 11 is not integrated with the filter element 5 at the inside seal part 13, that is, since the second container forming part 11 is not sealed to the filter element 5, there is the advantage that arrangement of the outlet port 11a in the step of sealing the outlet port 11a to the second container forming part 11 can be performed with a comparatively high degree of freedom. More specifically, sealing of the inlet port 9a and the outlet port 11a inside the flexible container 3 is an advantage of the process of manufacturing the container welding type blood processing filter 1A in which forming the inside seal part 13 and the outside seal part 15 by a simple step is a feature, and by adopting a configuration in which the inside seal part 13 does not seal the second container forming part 11 it is possible to provide an even greater degree of freedom with respect to arrangement of the outlet port 11a.

Figure 4:
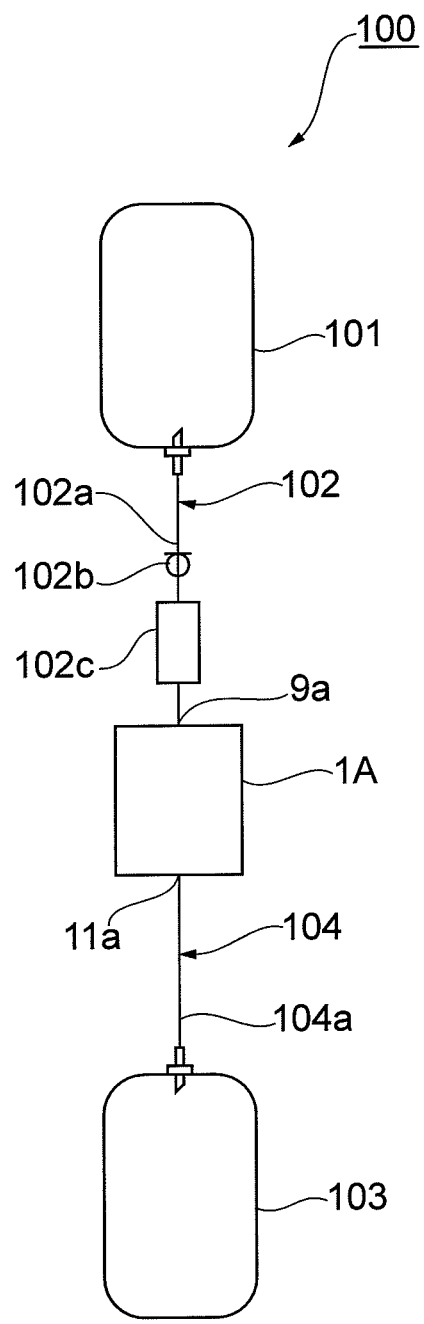
FIG. 4 is a front view that shows an outline of a blood processing system that includes the blood processing filter according to the first embodiment.

Next, a blood processing system 100 that includes the blood processing filter 1A is described (see FIG. 4).

The blood processing filter 1A can be used for filtering using gravity. For example, the blood processing system 100 to which the blood processing filter 1A is applied includes a reservoir bag 101 into which blood is filled after collection, the blood processing filter 1A, and a recovery bag 103 for accumulating blood after filtering. A preservative solution (priming fluid) for priming is previously inserted into the recovery bag 103. In this connection, although an example in which a preservative solution (priming fluid) for priming is previously inserted into the recovery bag 103 is described according to the present embodiment, a form may also be adopted in which a bag for a preservative solution is provided separately from the recovery bag 103, and priming is performed in a manner in which flow channels are appropriately switched.

The reservoir bag 101 and the inlet port 9a of the blood processing filter 1A are connected to each other by a capillary tube 102a such as a blood tube. The recovery bag 103 and the outlet port 11a of the blood processing filter 1A are connected to each other by a capillary tube 104a such as a blood tube. Opening/closing means 102b such as a roller clamp that opens and closes a flow channel, and a chamber 102c and the like are mounted to the capillary tube 102a on the upstream side. An inlet-side circuit 102 is formed by the capillary tube 102a, the opening/closing means 102b, and the chamber 102c and the like. An outlet-side circuit 104 is formed by the capillary tube 104a and the like on the downstream side.

Figure 5:
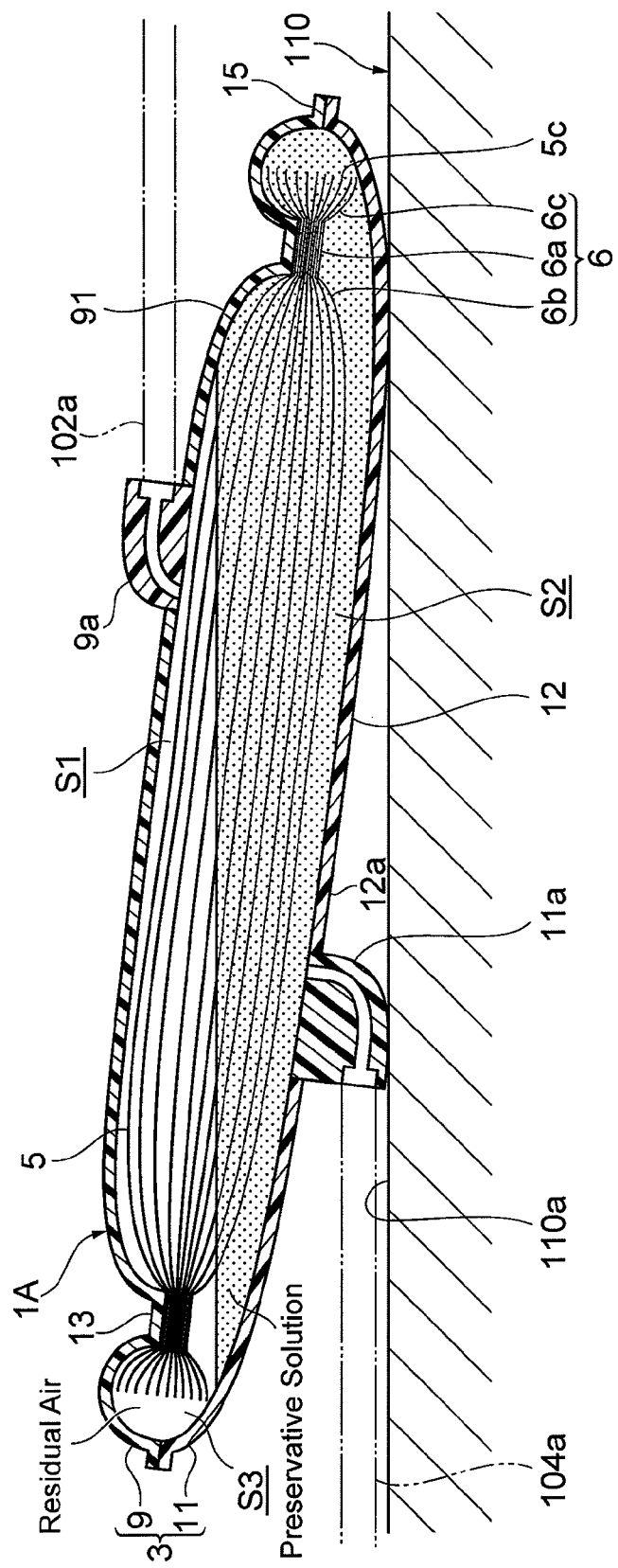
FIG. 5 is a sectional view that illustrates a state in which retro-priming is being performed with respect to the blood processing filter according to the first embodiment.
Figure 6:
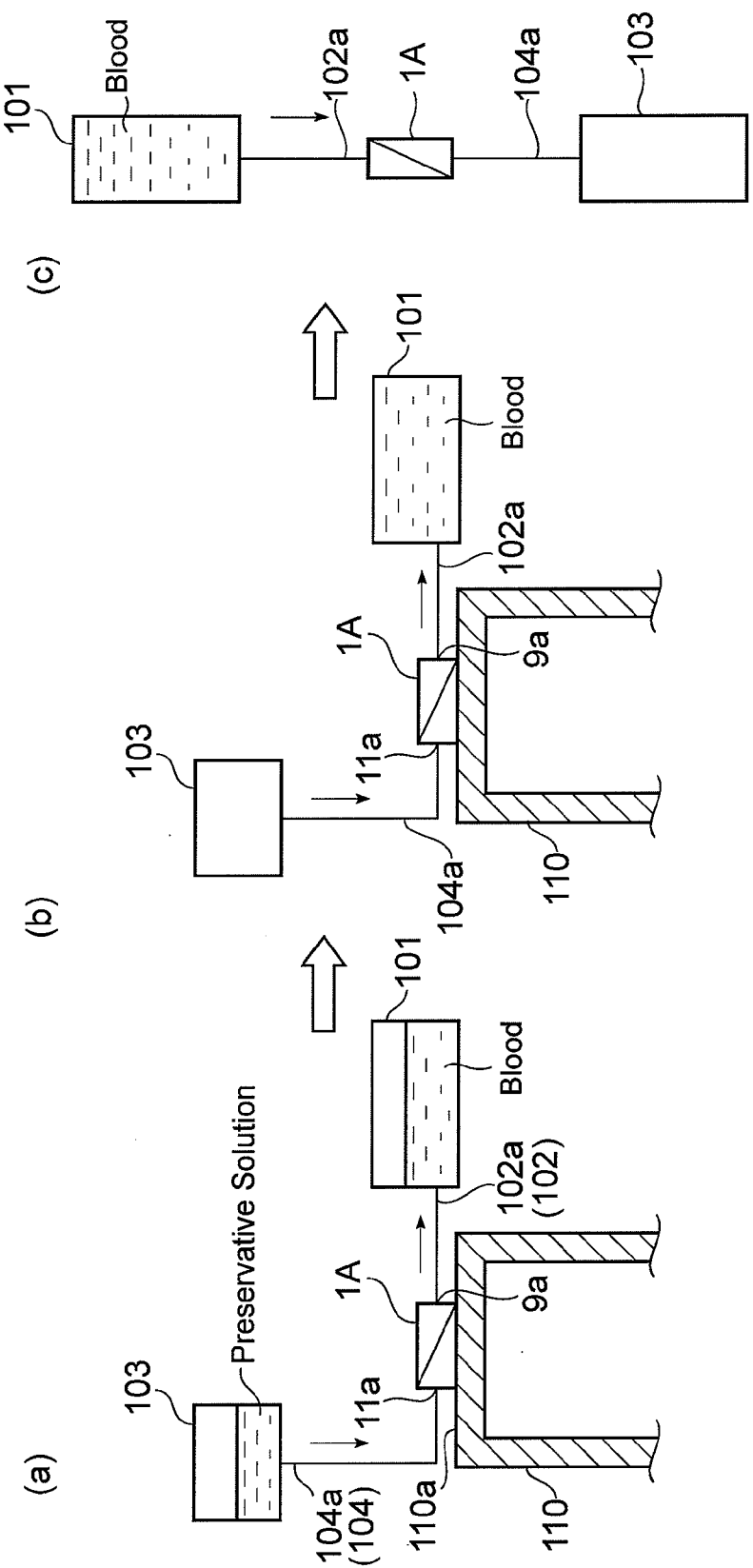
FIG. 6 is a view that schematically illustrates procedures in which retro-priming is performed with respect to a blood processing filter, and thereafter a filtration process is performed, in which: (a) is a view that illustrates a state in which retro-priming is being performed, (b) is a view that illustrates a state in which retro-priming is completed, and (c) is a view that illustrates an initial state after transitioning to the filtration process.

Next, a method for priming the blood processing filter 1A is described referring to FIG. 5 and FIG. 6. Prior to performing processing of blood in order to remove leukocytes or the like, it is necessary to extract air from inside the blood processing filter 1A and wet the filter element 5. Retro-priming is performed for this purpose.

When performing retro-priming with respect to the blood processing filter 1A, the blood processing filter 1A is turned sideways in a state in which the outlet side faces downwards, and is set on a mounting face 110a of a substantially horizontal stand 110. The outlet port 11a that protrudes from the outer surface 12a of the extension space forming part 12 of the second container forming part 11 is provided in the blood processing filter 1A. Consequently, when the blood processing filter 1A whose outlet side is facing downward is set on the mounting face 110a of the stand 110, the outlet port 11a comes between the outer surface of the blood processing filter 1A and the mounting face 110a, and thus the blood processing filter 1A enters an inclined state (see FIG. 5). As a result, one portion of the surrounding space forming part 92 that encloses the filtration space forming part 91 in a ring shape is positioned above the filtration space forming part 91.

Next, the recovery bag 103 is arranged at a position that is above the blood processing filter 1A, the reservoir bag 101 is arranged at a position that is below the blood processing filter 1A (see FIG. 6(a) and FIG. 6(b)), and the inlet-side circuit 102 and the outlet-side circuit 104 are opened. The preservative solution (priming fluid) for diluting the blood is inside the recovery bag 103, and when the recovery bag 103 is arranged at a higher position than the blood processing filter 1A the preservative solution inside the recovery bag 103 flows as far as the blood processing filter 1A through the capillary tube 104a, and passes through the outlet port 11a and is filled into the filtration space S2 on the outlet side within the flexible container 3. The boundary surface of the preservative solution rises as the preservative solution is being filled, and as a result the air inside the flexible container 3 passes through the filter element 5 and is pushed out from the inlet port 9a to thereby remove air from the blood processing filter 1A.

When air is pushed out from the inlet port 9a as described above, some air also stays behind in a space on the outlet side of the filter element 5. However, because the air accumulating space S3 exists above the filtration space S2 on the outlet side, the residual air escapes into the air accumulating space S3, and therefore the occurrence of air block in the filtration space S2 on the outlet side can be suppressed and removal of air can be performed smoothly.

In particular, in the blood processing filter 1A according to the present embodiment, the outlet port 11a is arranged inside the region Ar that overlaps with the filtration space forming part 91. That is, the outlet port 11a is arranged at a position that is comparatively near the center, and not the periphery, of the extension space forming part 12. Therefore the blood processing filter 1A inclines to a large degree. Accordingly, the escape of residual air into the air accumulating space S3 is promoted, and the suppression of an air block inside the filtration space S2 on the outlet side and the smooth removal of air are performed more efficiently.

After air has been pushed out from inside the flexible container 3, the preservative solution passes through the inlet port 9a and flows out into the capillary tube 102a, and ultimately reaches the reservoir bag 101. Thus, the retro-priming ends.

After the end of retro-priming, normal blood processing (a filtration process) for the purpose of removing leukocytes or the like is performed (see FIG. 6(c)). In the case of normal blood processing, the reservoir bag 101 into which blood is filled after collection is arranged at a position that is approximately 50 cm higher than the blood processing filter 1A, and the recovery bag 103 in which blood is accumulated after filtering is arranged at a position that is approximately 100 cm lower than the blood processing filter 1A.

The blood filtering process is performed by opening the flow channel of the blood processing system 100. When performing a filtering process (at a time of use), a negative pressure arises on the outlet side of the flexible container 3 of the blood processing filter 1A, and the second container forming part 11 deforms and adheres to the filter element 5. However, the valley part 6 is formed on the outlet side of the filter element 5, and the outer slanted face portion 6c (protruding nonwoven fabric portion 5c) of the valley part 6 comes between the filter element 5 and the second container forming part 11 so that adherence of the second container forming part 11 to the filter element 5 is partially restricted, and therefore the passage region Ps formed by the valley part 6 is maintained as a gap. As a result, it is difficult for the blood flow channel to be blocked, and it is easy to stably maintain the blood flow channel on the outlet side of the blood processing filter 1A.

Next, the actions and effects of the blood processing filter 1A according to the present embodiment are described. In the case of the blood processing filter 1A, an area surrounded by the inside seal part 13 of the filter element 5 functions as the effective filtering portion 5a of the filter element 5. Further, although the filtration space S1 on the inlet side of the flexible container 3 is a narrow space that substantially faces the effective filtering portion 5a, the space on the outlet side is a wide space that includes not only the narrow filtration space S1 that faces the effective filtering portion 5a, but also the surrounding extended air accumulating space S3. Since the wide space side is the outlet side for blood, the occurrence of an air block due to a build-up of air bubbles at the surface on the outlet side of the filter element 5 can be prevented when priming the blood processing filter 1A, and the filter performance can be improved.

Figure 7:
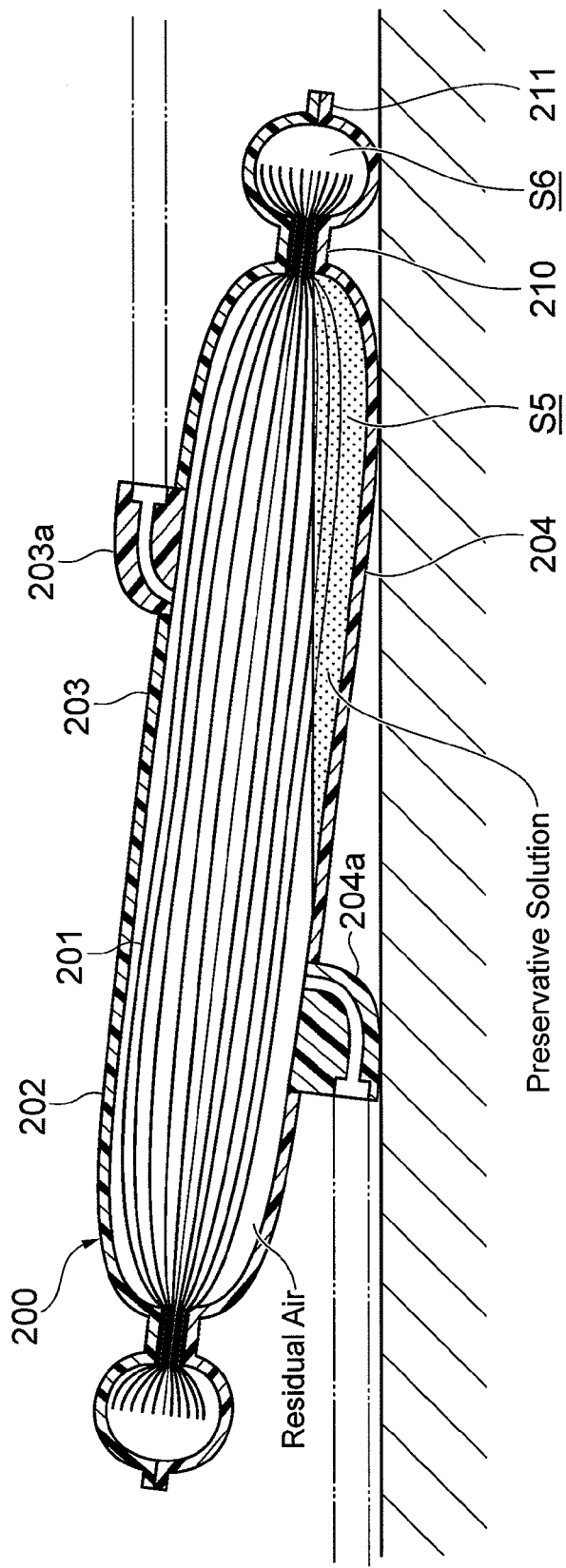
FIG. 7 is a sectional view of a reference example of a blood processing filter, that illustrates a state in which retro-priming is being performed with respect to the blood processing filter according to the reference example.

The above described effect will now be described while referring to and comparing FIG. 5 and FIG. 7. FIG. 5 is a sectional view of the blood processing filter according to the present embodiment, and FIG. 7 is a sectional view of a blood processing filter according to a reference example. A blood processing filter 200 according to the reference example includes a sheet-like filter element 201, and a flexible container 202 whose internal space is divided into an inlet side and an outlet side by the filter element. The flexible container 202 has a first container forming part 203 and a second container forming part 204 that are arranged opposite each other so as to sandwich the filter element 201 therebetween. An inlet port 203a is provided in the first container forming part 203, and an outlet port 204a is provided in the second container forming part 204.

The first container forming part 203 and the second container forming part 204 are integrated with the filter element 201 at both an inside seal part 210 and an outside seal part 211. That is, unlike the second container forming part 11 according to the present embodiment, in the second container forming part 204 according to the reference example, a filtration space S5 and a surrounding space S6 are clearly separated by the inside seal part 210.

As shown in FIG. 7, when performing retro-priming with respect to the blood processing filter according to the reference example, there is no way for air that remains inside the filtration space S5 on the outlet side to escape, and there is the possibility of producing an air block. In contrast, in the case of the blood processing filter 1A according to the present embodiment, as shown in FIG. 5, the residual air escapes to the air accumulating space S3 that is located away from the effective filtering portion 5a of the filter element 5. Accordingly, it is possible to prevent an air block from occurring due to air bubbles accumulating at the surface on the outlet side of the filter element 5, and thus filter performance can be improved.

Further, since the valley part 6 that is partially recessed on the outlet side of the filter element 5 is formed in the blood processing filter 1A, there is an advantage at a time of normal filtration also. More specifically, since the valley part 6 is formed around the effective filtering portion 5a, the flow of blood to the valley part 6 as a blood flow channel from the filter element 5 on the outlet side spreads out and does not concentrate at one point. Accordingly, even if a dual force caused by a positive pressure on the inlet side and a negative pressure on the outlet side acts at the time of filtering, it is possible to avoid a situation in which the flow of blood is inhibited by adherence or the like between the second container forming part 11 and the filter element 5 and the filtering performance is lowered. This is advantageous in terms of effectively utilizing the entire filter element 5, and thus both a high filtering flow rate and high filtering performance can be achieved in a compatible manner.

Figure 8:
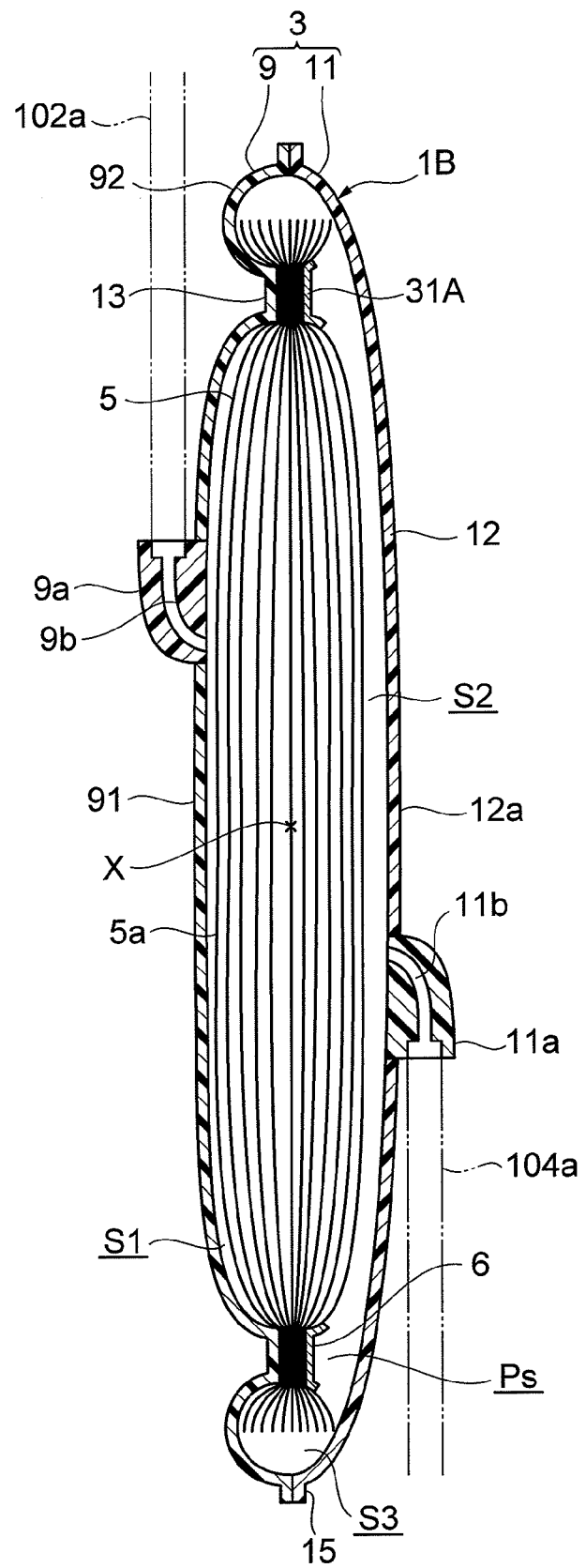
FIG. 8 is a sectional view of a blood processing filter according to a second embodiment.

Next, a blood processing filter according to a second embodiment of the present invention is described referring to FIG. 8. FIG. 8 is a sectional view of the blood processing filter according to the second embodiment of the present invention. In this connection, a blood processing filter 1B according to the second embodiment includes substantially the same elements and structures as the blood processing filter 1A according to the first embodiment. Hence, in the following description, elements and structures that are the same as in the first embodiment are denoted by the same reference symbols and a detailed description thereof is omitted, and the description centers on elements and structures that are different from those of the first embodiment.

The blood processing filter 1B includes a flexible container 3 that has an inlet port 9a and an outlet port 11a for blood, a sheet-like filter element 5 that is arranged so as to divide an internal space of the flexible container 3 into an inlet port 9a side and an outlet port 11a side, and a welding sheet 31A that is arranged on the outlet side of the filter element 5 at a position that corresponds to a position at which the inside seal part 13 is formed. The flexible container 3 includes a first container forming part 9 having a rectangular sheet shape, and a second container forming part 11 having a rectangular sheet shape.

The first container forming part 9 and the second container forming part 11 overlap with each other through the rectangular filter element 5. The first container forming part 9, the filter element 5, and the welding sheet 31A are sealed to each other and thereby integrated, and as a result a band-shaped inside seal part 13 is formed along the periphery of the filter element 5. The valley part 6 is formed in the filter element 5 by the inside seal part 13, and in a state in which blood is flowing (state at a time of use), a passage region Ps is formed between the valley part 6 and the second container forming part 11.

In the blood processing filter 1B according to the present embodiment, a space on the outlet side is a wide space that includes not only a narrow filtration space S2 facing the effective filtering portion 5a, but also a surrounding extended air accumulating space S3. Since the wide space side is the outlet side for blood, the occurrence of an air block due to a build-up of air bubbles at the surface on the outlet side of the filter element 5 can be prevented when priming the blood processing filter 1B, and thus the filter performance can be improved.

Further, even if a dual force caused by a positive pressure on the inlet side and a negative pressure on the outlet side acts at the time of filtering, it is possible to avoid a situation in which the flow of blood is inhibited by adherence or the like between the second container forming part 11 and the filter element 5 and the filtering performance is lowered. This is advantageous in terms of effectively utilizing the entire filter element 5, and thus both a high filtering flow rate and high filtering performance can be achieved in a compatible manner.

Figure 9:
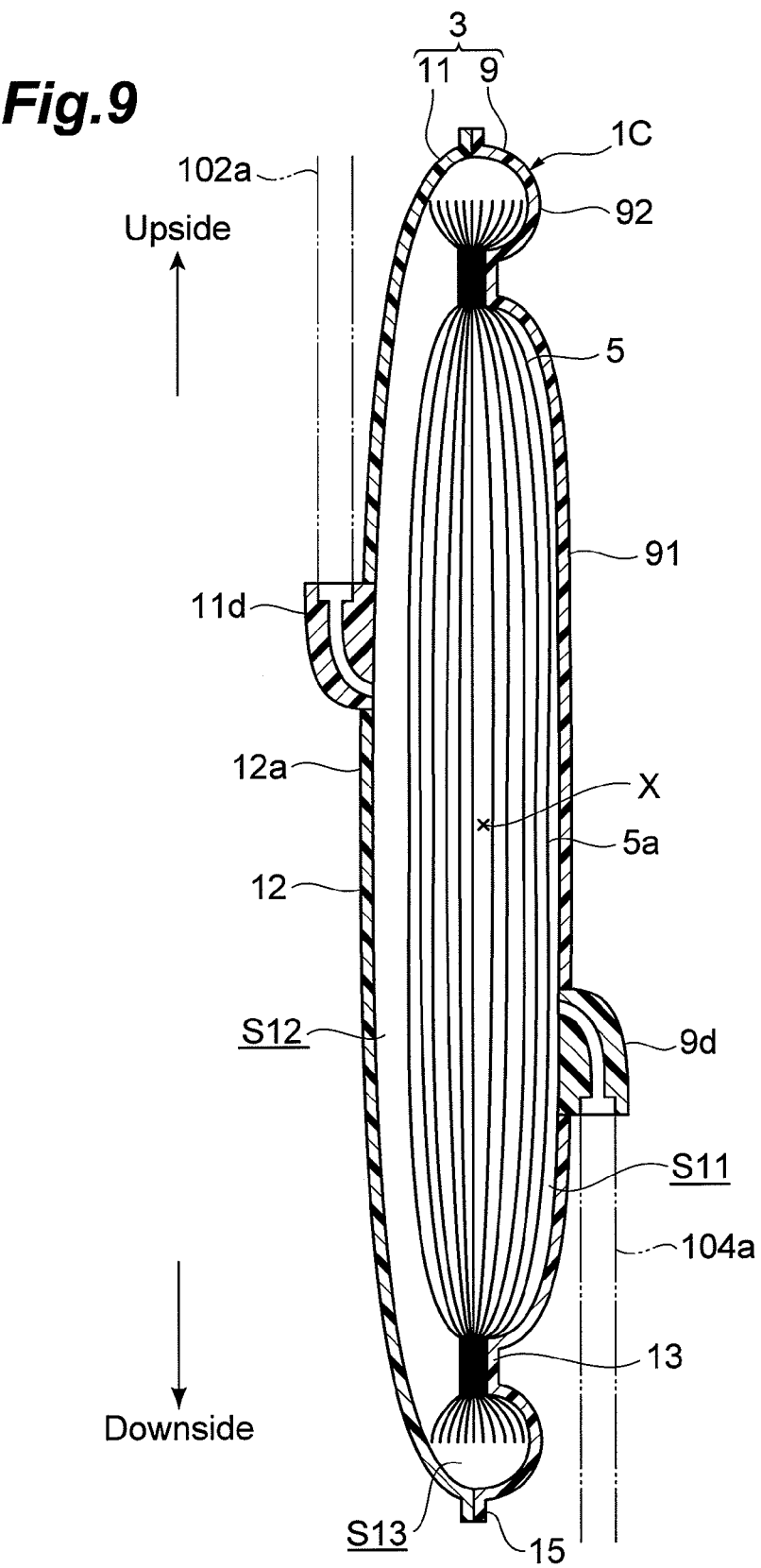
FIG. 9 is a sectional view of a blood processing filter according to a third embodiment.

Next, a blood processing filter according to a third embodiment of the present invention is described referring to FIG. 9.

FIG. 9 is a sectional view of the blood processing filter according to the third embodiment of the present invention, and shows a state in which the blood processing filter is placed in an upright state to perform a normal filtration process. The substantial point of difference between a blood processing filter 1C according to the third embodiment and the blood processing filter 1A according to the first embodiment is that the positions of the inlet port and the outlet port are reversed. Hence, the following description centers on this point of difference, and elements and structures that are substantially the same as in the first embodiment are denoted by the same reference symbols and a detailed description thereof is omitted.

The blood processing filter 1C includes a flexible container 3 that has an inlet port 11d and an outlet port 9d for blood, and a sheet-like filter element 5 that is arranged so as to divide an internal space of the flexible container 3 into one side and another side.

The flexible container 3 includes a first container forming part 9 having a rectangular sheet shape, and a second container forming part 11 having a rectangular sheet shape. The outlet port 9d is formed in the first container forming part 9, and the inlet port 11d is formed in the second container forming part 11. The first container forming part 9 and the second container forming part 11 are arranged opposite each other so as to sandwich the filter element 5 therebetween. Of the two sides into which the flexible container 3 is divided by the filter element 5, the outlet port 9d communicates with an internal space on the one side, and the inlet port 11d communicates with an internal space on the other side.

The flexible container 3 has an annular inside seal part (first seal part) 13 and an annular outside seal part (second seal part) 15. The inside seal part (first seal part) 13 is formed so as to seal the first container forming part 9 and the filter element 5 in a band shape and surround the outlet port 9d provided in the first container forming part 9. The outside seal part (second seal part) 15 is formed so as to seal the first container forming part 9 and the second container forming part 11, and surround the inside seal part 13 along an outer edge of the second container forming part 11.

The first container forming part 9 has an interior filtration space forming part 91 and an exterior surrounding space forming part 92 that are separated by the inside seal part 13. The second container forming part 11 has an extension space forming part 12 that is surrounded by the outside seal part 15, and is arranged opposite the filter element 5 and the surrounding space forming part 92 without being divided by the inside seal part 13. The inlet port 11d of the second container forming part 11 is provided in the extension space forming part 12, and protrudes further than an outer surface 12a of the extension space forming part 12.

In the blood processing filter 1C, an area surrounded by the inside seal part 13 of the filter element 5 functions as an effective filtering portion 5a of the filter element 5. Although a filtration space S11 on the outlet side of the flexible container 3 is a narrow space that substantially faces the effective filtering portion 5a, a space on the inlet side is a wide space that includes not only a narrow filtration space S12 that faces the effective filtering portion 5a, but also a surrounding extended surplus space S13. Since the wide space side is the inlet side for blood, for example, even if aggregates or air bubbles enter during filtration, the aggregates or air bubbles escape into the surrounding surplus space S13 that is located away from the effective filtering portion 5a, and thus blocking of the filter element 5 can be suppressed and filter performance can be improved.

Accordingly, for example, even when blood with respect to which generation of aggregates is a concern is processed, such as when the blood has been stored in refrigerated storage for a fixed period of time, since a wide space is formed on the inlet side, the possibility of aggregates or the like attaching to the filter element 5 and blocking the filter element 5 can be reduced.

Figure 10:
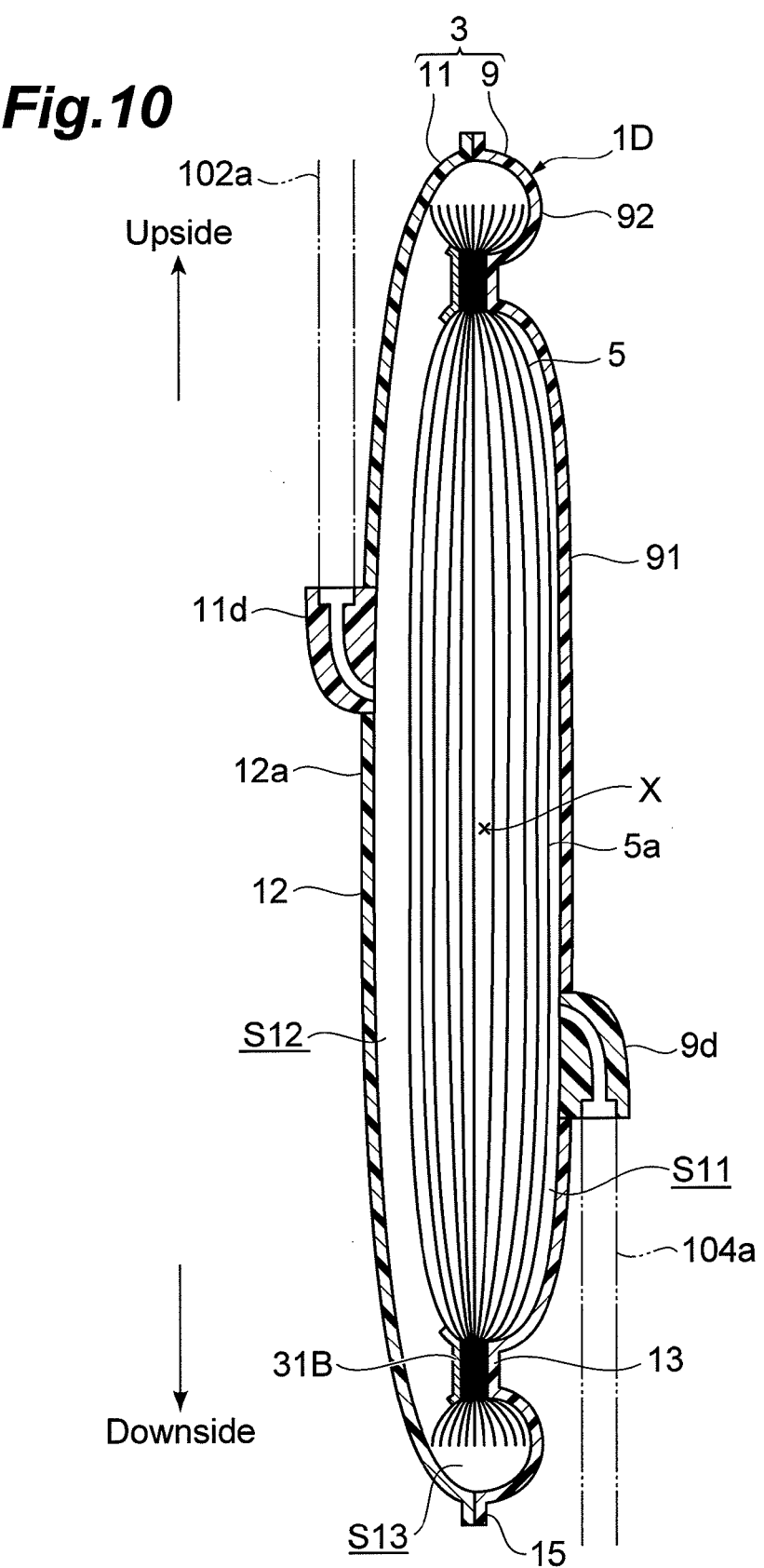
FIG. 10 is a sectional view of a blood processing filter according to a fourth embodiment.

Next, a blood processing filter according to a fourth embodiment of the present invention is described referring to FIG. 10. FIG. 10 is a sectional view of the blood processing filter according to the fourth embodiment of the present invention, and shows a state in which the blood processing filter is placed in an upright state to perform a normal filtration process. A blood processing filter 1D according to the fourth embodiment includes substantially the same elements and structures as the blood processing filter 1C according to the third embodiment. Hence, in the following description, elements and structures that are the same as in the third embodiment are denoted by the same reference symbols and a detailed description thereof is omitted, and the description centers on elements and structures that are different from those of the third embodiment.

The blood processing filter 1D includes a welding sheet 31B that is arranged on an inlet side of a filter element 5 at a position corresponding to a position at which an inside seal part 13 is formed.

A first container forming part 9 and a second container forming part 11 overlap with each other so as to sandwich the rectangular filter element 5. The first container forming part 9, the filter element 5, and the welding sheet 31B are sealed to each other and thereby integrated, and as a result the band-shaped inside seal part 13 is formed along the periphery of the filter element 5. A valley part 6 is formed in the filter element 5 by the inside seal part 13, and in a state in which blood is flowing (state at a time of use), a passage region Ps is formed between the valley part 6 and the second container forming part 11.

In the blood processing filter 1D, an area surrounded by the inside seal part 13 of the filter element 5 functions as an effective filtering portion 5a of the filter element 5. Although a filtration space S11 on the outlet side of the flexible container 3 is a narrow space that substantially faces the effective filtering portion 5a, a space on the inlet side is a wide space that includes not only a narrow filtration space S12 that faces the effective filtering portion 5a, but also a surrounding extended surplus space S13. Since the wide space side is the inlet side for blood, for example, even if aggregates or air bubbles enter during filtration, the aggregates or air bubbles escape into the surrounding surplus space S13 that is located away from the effective filtering portion 5a, and thus blocking of the filter element 5 can be suppressed and filter performance can be improved.

Accordingly, for example, even when blood with respect to which generation of aggregates is a concern is processed, such as when the blood has been stored in refrigerated storage for a fixed period of time, since a wide space is formed on the inlet side, the possibility of aggregates or the like attaching to the filter element 5 and blocking the filter element 5 can be reduced.

EXAMPLES

The present invention will now be described in further detail below by way of examples. However, the following examples should not be construed as limiting the present invention.

Example 1

A blood processing filter including a filter element and a flexible container having a container forming part on an inlet side (first container forming part) and a container forming part on an outlet side (second container forming part) was prepared, and an inlet port thereof was connected to a reservoir bag via an inlet-side circuit having a length of 50 cm. An outlet port of the filter was connected to a recovery bag including 100 mL of red cell preservative solution (SAG-M) via an outlet-side circuit having a length of 100 cm. A tube made of soft polyvinyl chloride having an internal diameter of 2.9 mm and an external diameter of 4.2 mm was used for the inlet-side circuit and the outlet-side circuit.

In preparing the blood processing filter, an effective filtering portion was formed in a rectangular shape in which an inner side of a first seal part had a longitudinal dimension of 74 cm and a horizontal dimension of 57 cm, a corner portion was formed as a curve, and an effective filtration area of $42 \times 10^{-4}$ ($m^2$) was provided. As the filter element, four sheets of polyester nonwoven fabric having an air permeability of 237.3 (cc/$cm^2$/sec) and a thickness of 0.2 mm, one sheet of polyester nonwoven fabric having an air permeability of 8.4 (cc/$cm^2$/sec) and a thickness of 0.4 mm, 32 sheets of polyester nonwoven fabric having an air permeability of 7.7 (cc/$cm^2$/sec) and a thickness of 0.20 mm, one sheet of nonwoven polyester fabric having an air permeability of 8.4 (cc/$cm^2$/sec) and a thickness of 0.4 mm, and four sheets of nonwoven polyester fabric having an air permeability of 237.3 (cc/$cm^2$/sec) and a thickness of 0.2 mm were stacked in that order from the inlet to the outlet at the time of filtering blood, and used. In this connection, the air permeability was measured by a method based on Japanese Industrial Standard JIS L-1096, 6.27.1A.

The two ports serving as the inlet and the outlet were sealed in separate container forming parts, respectively. The first seal part was formed by disposing one of the container forming parts and the filter element in a layered arrangement. Thereafter, the other container forming part was arranged so as to sandwich the filter element between the two container forming parts, and the peripheries of the two container forming parts were caused to overlap with each other to form the second seal part. At that time, sealing and assembly were performed so as to dispose the openings of the respective ports at positions on the inner side of the filtering part which were 2.4 cm from an end on the effective filtering portion side of a short side portion of the rectangular-shaped first seal part. The port provided in the container forming part welded to the filter element at the first seal part was taken as the inlet side port and connected to a circuit (inlet-side circuit) on the side that was connected to the reservoir bag. The port on the opposite side was taken as the outlet side port and connected to a circuit (outlet-side circuit) on the side that was connected to the recovery bag.

The recovery bag was suspended so that a drop from a circuit connection part of the recovery bag to the horizontally placed blood processing filter was 50 cm, the blood processing filter and the reservoir bag were placed on a table, and the filter was primed with the red cell preservative solution. At that time, the port on the side serving as an inlet for the red cell preservative solution (side serving as the outlet side at the time of blood filtration) was arranged on the bottom side so as to contact the table.

After the red cell preservative solution had completely flowed from the recovery bag into the reservoir bag, the reservoir bag including the red cell preservative solution used for priming was exchanged for another reservoir bag including a liquid to be processed (a blood substitute) and a sterile connecting device. At that time, the length of the circuit was maintained without change.

As the liquid to be processed (blood substitute), 300 g of an aqueous solution of polyvinyl pyrrolidone (weight average molecular weight: 360,000) adjusted to a viscosity of 17 mPa·s (25° C.) and pH 3.8 was used at room temperature. The total drop from the reservoir bag to the recovery bag was fixed at 150 cm. The recovery bag was placed in advance on a scale balance to enable verification of changes in the weight thereof, and the liquid to be processed was filtered using gravity.

At this time, a time required from when the liquid to be processed started to flow until all of the liquid to be processed was discharged from inside the reservoir bag and a converted weight of the post-filtration liquid recovery bag ceased to increase, more specifically, the time required to filter all of the liquid, was measured, and the measured time was defined as a total processing time (minutes). The same test was repeated ten times.

Comparative Example 1

Filtering was carried out using a filter assembled by the same method as in Example 1, except that a first seal part was formed by sandwiching a filter element between two container forming parts, and thereafter a second seal part was formed by sandwiching the filter element between two container forming parts.

Table 1 shows the results for Example 1 and Comparative Example 1.

TABLE 1

|  |  | Example 1 | Comparative Example 1 |
|---|---|---|---|
| Total Processing Time (min) | Number of Tests | 10 | 10 |
|  | Mean | 26.3 | 32.2 |
|  | Standard Deviation | 1.5 | 11.6 |

Example 2

Assembly of a blood processing filter, and connection of an inlet-side container and an outlet-side container were carried out according to the same method as in Example 1, except that: the port provided in the container forming part welded to the filter element at the first seal part was taken as the outlet side port and connected to a circuit (outlet-side circuit) on the side that was connected to the recovery bag; the port on the opposite side was taken as the inlet side port and connected to a circuit (inlet-side circuit) on the side that was connected to the reservoir bag; the reservoir bag included the liquid to be processed; and an empty container that did not include a red cell preservative solution was used as the recovery bag.

The total drop from the reservoir bag to the recovery bag was fixed at 150 cm. The recovery bag was placed in advance on a scale balance to enable verification of changes in the weight thereof, and the liquid to be processed was filtered using gravity.

The liquid to be processed was obtained by adding 70 mL of anticoagulant solution (CPD-A) to 500 mL of pig whole blood and mixing, and thereafter storing the resulting product in a flexible container at 4° C. for three days before use. After taking the liquid to be processed out from a cooling box, blood cell components and liquid components that had separated during storage were mixed by inversion, and thereafter filtration was carried out forthwith.

At this time, a time required from when the liquid to be processed started to flow until all of the liquid to be processed was discharged from inside the reservoir bag and a converted weight of the post-filtration liquid recovery bag ceased to increase, more specifically, the time required to filter all of the liquid, was measured, and the measured time was defined as a total processing time (minutes). The same test was repeated ten times.

Comparative Example 2

Filtering was carried out using a filter assembled by the same method as in Example 2, except that a first seal part was formed by sandwiching a filter element between two container forming parts, and thereafter a second seal part was formed by sandwiching the filter element between two container forming parts.

Table 2 shows the results for Example 2 and Comparative Example 2.

TABLE 2

|  |  | Example 2 | Comparative Example 2 |
|---|---|---|---|
| Total Processing Time (min) | Number of Tests | 10 | 10 |
|  | Mean | 44.3 | 63.1 |
|  | Standard Deviation | 4.1 | 31.1 |

What is claimed is:

1. A method for priming a blood processing filter comprising a sheet-like filter element, and a flexible container having an internal space that is divided into one side and another side by the filter element, the flexible container comprising: a first container forming part and a second container forming part that are arranged opposite each other so as to sandwich the filter element therebetween, an inlet port that is provided in the first container forming part and that serves as an inlet for blood, an outlet port that is provided in the second container forming part and that serves as an outlet for blood, a band-shaped annular first seal part that seals the first container forming part and the filter element and that is formed so as to surround the inlet port, and an annular second seal part that seals at least the first container forming part and the second container forming part and that is formed so as to surround the first seal part along an outer edge of the second container forming part;

wherein:

the first container forming part has an interior filtration space forming part and an exterior surrounding space forming part that are separated by the first seal part, and the second container forming part has an extension space forming part that is surrounded by the second seal part and is arranged opposite the filter element and the surrounding space forming part, without being divided by the first seal part; and the inlet port is provided in the filtration space forming part and communicates with an internal space on the one side that is defined by the filter element, and the outlet port is provided in the extension space forming part and communicates with an internal space on the other side that is defined by the filter element and protrudes further than an outer surface of the extension space forming part;

the method comprising:

turning the blood processing filter sideways with the outlet port facing downwards, and setting the blood processing filter on a mounting face in a state in which blood processing filter is inclined with respect to the mounting face; and filling a priming fluid from the outlet port of the blood processing filter that is set on the mounting face to remove air from inside the blood processing filter.

2. The method for priming a blood processing filter according to claim 1, wherein the port of the first container forming part is an inlet port that serves as an inlet for blood, and the port of the second container forming part is an outlet port that serves as an outlet for blood.

3. The method for priming a blood processing filter according to claim 1, wherein the port of the first container forming part is an outlet port that serves as an outlet for blood, and the port of the second container forming part is an inlet port that serves as an inlet for blood.

4. The method for priming a blood processing filter according to claim 2, wherein, the outlet port is arranged in a region of the extension space forming part that overlaps with the filtration space forming part.

5. The method for priming a blood processing filter according to claim 2, wherein the inlet port and the outlet port are point symmetric.

* * * * *